United States Patent [19]

LeRoy

[11] 4,068,655
[45] Jan. 17, 1978

[54] SURGICAL RETRACTOR AND SPONGE CARRYING ASSEMBLY

[75] Inventor: Pierre L. LeRoy, Wilmington, Del.

[73] Assignee: New Research and Development Lab., Inc., Wilmington, Del.

[21] Appl. No.: 710,735

[22] Filed: Aug. 2, 1976

[51] Int. Cl.² .............................................. A61B 17/02
[52] U.S. Cl. .................................. 128/20; 128/132 D; 128/290 R; 128/157; 128/1 R
[58] Field of Search ................... 128/1 R, 20, 132 D, 128/133, 287, 290 R, 292, 325, 155, 156, 157, 296; 248/1

[56] References Cited

U.S. PATENT DOCUMENTS

| | | | |
|---|---|---|---|
| 2,219,974 | 10/1940 | Bellow | 248/1 |
| 3,372,696 | 3/1968 | Rudie | 128/132 D |
| 3,563,242 | 2/1971 | Hedstrom et al. | 128/290 R |
| 3,948,390 | 4/1976 | Ferreri | 128/296 |
| 3,986,505 | 10/1976 | Power | 128/157 |

*Primary Examiner*—Stephen C. Pellegrino
*Assistant Examiner*—Henry S. Layton
*Attorney, Agent, or Firm*—Connolly and Hutz

[57] ABSTRACT

A surgical retractor and sponge carrying assembly particularly adapted for craniotomies includes a flexible retractor member which is wrapped around the wound flap to hold the wound flap retracted and also to function as a hemostatic device. An intermediate conformable member such as a bean bag is mounted on the retractor member for providing a horizontal support surface to which a sponge carrying tray may be secured.

16 Claims, 9 Drawing Figures

U.S. Patent  Jan. 17, 1978  Sheet 1 of 2  4,068,655
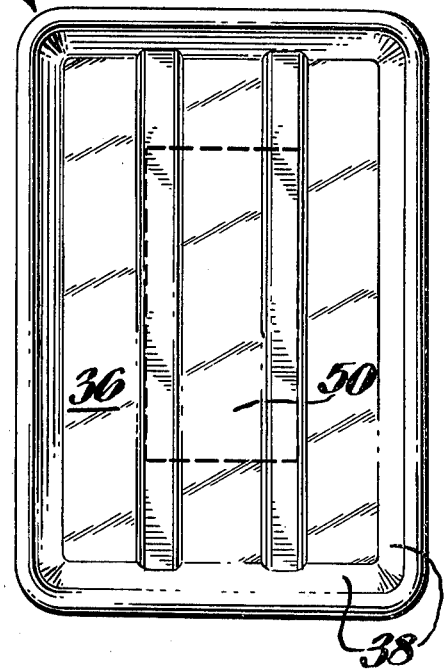
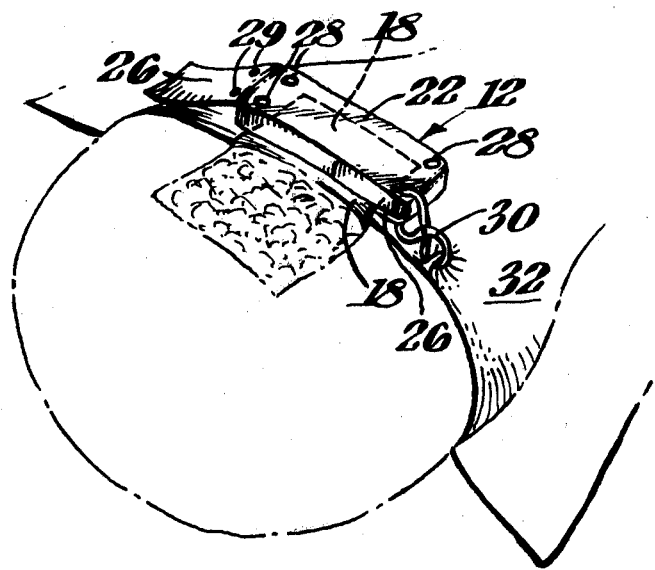
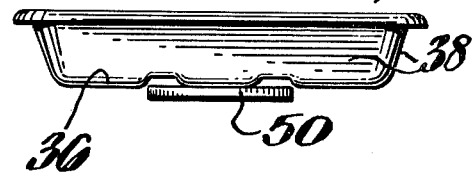
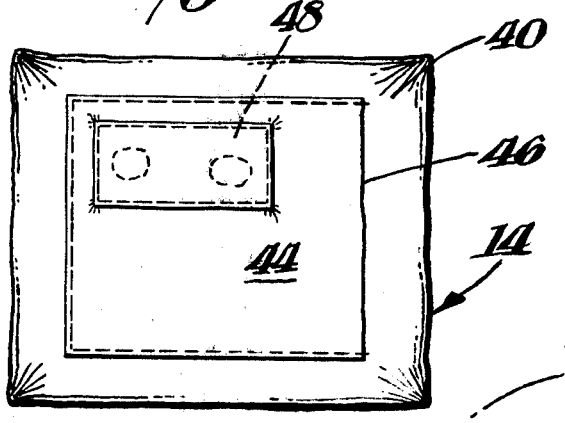
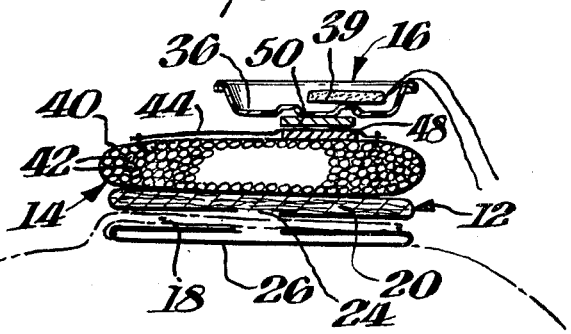

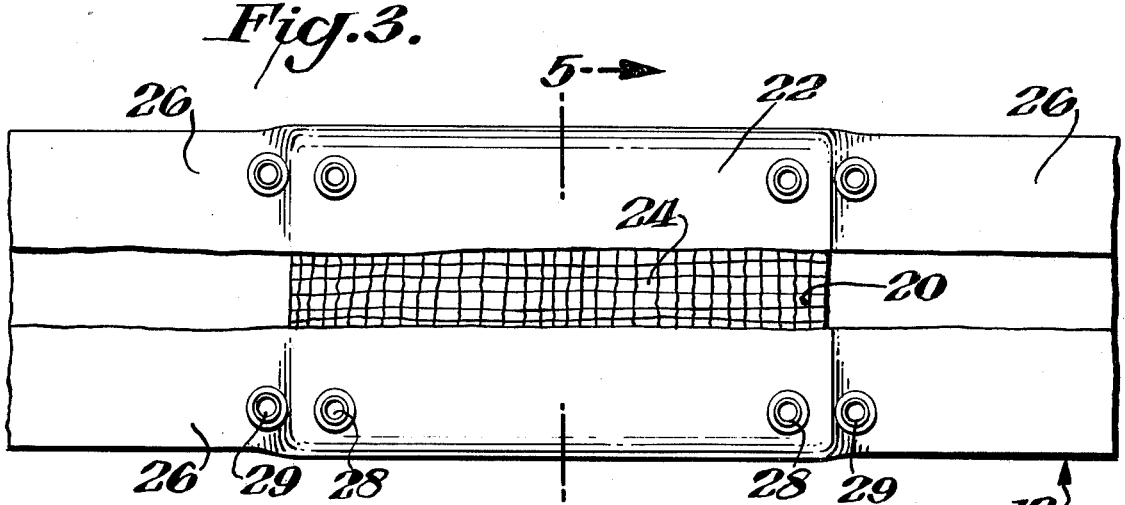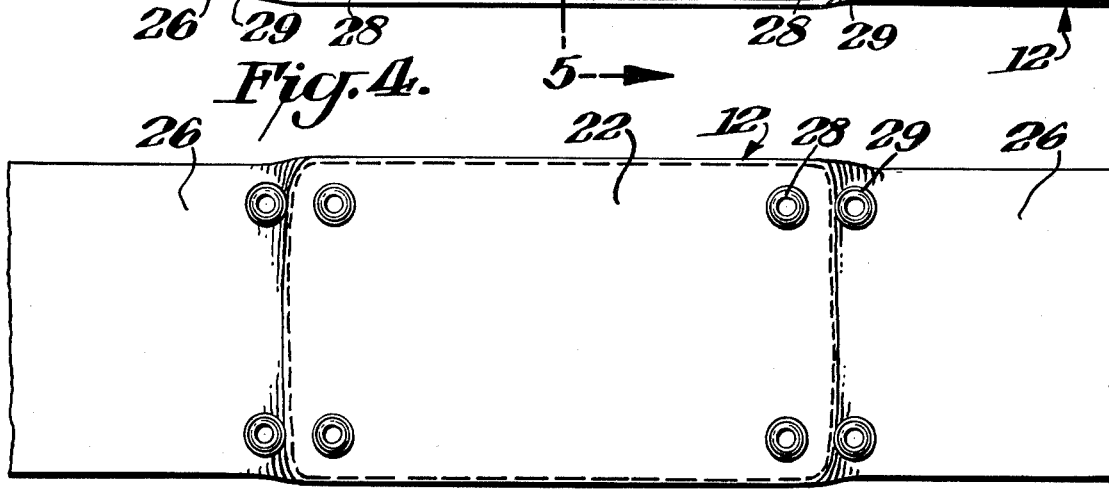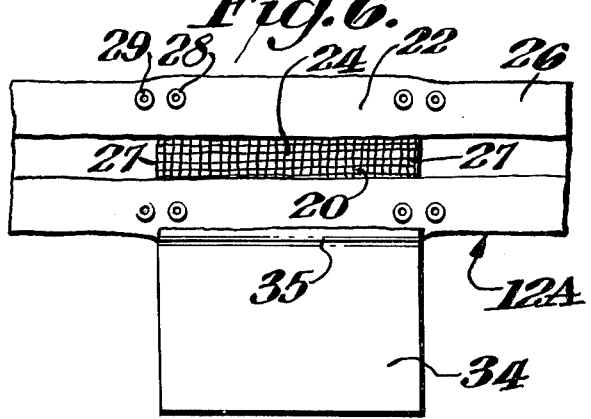

SURGICAL RETRACTOR AND SPONGE CARRYING ASSEMBLY

BACKGROUND OF THE INVENTION

In most surgical operations, particularly cranial operations, time is of the essence. Such operative procedures require the use of moist sponges or pads and at the termination of the operation a sponge count is made to assure that no such sponges were inadvertently left in the operative site.

It is common practice in, for example, cranial operations to hold the osteo plastic flap retracted by the use of rubber bands and/or towel clips or gauze strips clamped to the surgical drapes or other supports. Such techniques, however, are both cumbersome and undesirable.

It is further common under present practices to require a nurse for supplying the sponges or surgical pads which are generally located in a remote area. A water tray is also used to keep the pads moist. The disadvantages with such arrangements are self-evident from the added time and personnel requirements, as well as the inconvenience caused by remotely locating the pad supply and the water tray.

It would be desirable to provide a surgical retracting device which avoids the disadvantages generally attendant with the prior art. It would be further desirable to provide a convenient means to disposing moist sponges or pads as close to the operative site as possible.

SUMMARY OF THE INVENTION

An object of this invention is to provide a surgical retracting device which is capable of being quickly and conveniently applied to a wound flap.

A further object of this invention is to provide such a retracting device which also functions hemostatically.

A yet further object of this invention is to provide a moist sponge receptacle or tray at the operative site.

In accordance with this invention a surgical retractor and sponge carrying assembly includes a flexible retractor member which is wrapped around the wound flap to hold the wound flap retracted and also to function as a hemostatic device. An intermediate conformable support member, such as a bean bag, is mounted on the flexible member for providing a horizontal surface upon which a sponge carrying tray may be secured.

The retracting device may include a pad portion which is covered by a flexible extensible sterilizable non-conductive material such as a suitable presently available surgical rubber material. The pad itself is moisture absorbent for being in direct contact with and above the exposed inverted wound flap. Extensions or wing sections are provided on the pad cover for being tucked under the wound flap. Suitable securing means such as grommets may be provided at the corners of the pad for securement to a surgical drape. In this manner the device functions as a retractor.

The sponge carrying tray is disposed on the retracting member by being placed atop a pliable and conformable member, such as a bean bag, which in turn is positioned on the retracting member. The weight of the tray and bean bag upon and pad results in a hemostatic function for the assembly. Any suitable securing means may be utilized to assure a positive fixed mounting of the tray to the bean bag. Such means include, for example, magnets or formations of "Velero".

THE DRAWINGS

FIG. 1 is a perspective view illustrating the application of the retracting device to a wound flap;

FIG. 2 is an elevation view in section of the retractor and sponge carrying assembly of this invention;

FIG. 3 is a bottom plan view of the retracting device of FIGS. 1-2;

FIG. 4 is a top plan view of the retracting device of FIG. 3;

FIG. 5 is a cross-sectional view taken through FIG. 3 along the line 5—5;

FIG. 6 is a bottom plan view of an alternative form of retracting device in accordance with this invention;

FIG. 7 is a bottom plan view of a conformable support member of the assembly as illustrated in FIG. 2;

FIG. 8 is a top plan view of a sponge carrying device or tray of the assembly of FIG. 2; and FIG. 9 is an end elevation view of the tray of FIG. 8.

Detailed Description

FIG. 2 illustrates the components of the surgical retractor and sponge carrying assembly 10. Specifically assembly 10 includes a retractor member 12, an intermediate support member 14 and tray 16.

FIG. 1 is one exemplification of the use of the invention illustrating the retractor 12 being positioned in place. As schematically illustrated therein a cranical operation is being performed and a suitable incision is made which results in a flap 18 being created for exposing the specific area of the brain. It is to be understood, however, that the concepts of this invention may be applied for other types of surgery and is not limited to the illustrated example. Thus, the concepts of this invention may be used for such diverse operative sites as spinal operations.

FIGS. 3-5 show the details of retracting member 12. As illustrated therein, the central portion includes a relatively thick moisture absorbent pad 20 such as layers of conventional surgical cotton gauze. Pad 20 is covered by a flexible extensible or elastic material 22 such as suitable surgical rubber which is capable of being sterilized and which is non-conductive. Suitable materials include "Lycra" and other sheet rubber or similar elastic materials. As is apparent from FIGS. 3 and 5, the cover 22 is completely wrapped around one side of the gauze or pad 20 but leaves an open portion 24 on the lower surface of pad 22 for reasons which will later be explained. Cover 22 is made oversize so as to form a pair of wing sections or extensions 26 at each end thereof. Additionally, suitable securing means such as grommets 28 are provided at each corner of the pad 22. Grommets 28 serve multiple functions of securing the cover 22 and pad 20 together thus rendering the pad immobile with respect to the cover 22. Additionally, as later described grommets 28 cooperate with grommets 29 in wing sections 26 to provide a means of anchoring the retracting device 12 in place at the operative site.

With reference again to FIG. 1, in use the wound flap 18 is inverted with its inner surface thereby upwardly disposed in an exposed condition. Retracting member 12 is placed directly on top of the wound flap 18 with pad 20 in direct contact with the exposed inner surface of flap 18 by virtue of the exposed portion 24 of pad 20. In this manner the absorbent characteristics of pad 20 are utilized to absorb the fluid on wound flap 18. The extensions or wing sections 26 are then tucked under inverted flap 18 to assure a snug fitting of retracting member 12 around flap 18. FIG. 1 illustrates one of the extensions 26 already tucked under with the other extension 26 about to be tucked under. Edges 27 of pad 20 act as hinge areas about which extensions 26 are bent or folded. In this manner grommets 29 in extensions 26 are positioned in alignment with grommets 28. Any suitable securing means such as conventional towel clips 30 are inserted through grommets 28 and grommets 29 and secured to the surgical drape 32 or any other convenient suitable support thus holding retractor 12 in place which in turn maintains wound flap 18 in a retracted position.

FIG. 6 illustrates an alternative arrangement for the retracting device. As indicated therein, like numerals are used for like parts. Thus in addition to pad 20, cover 22 and wing sections 26, a further extension or wing section 34 is provided in the central region thereof. Retractor 12A would be applied in a manner similar to retractor 12 and additionally extension 34 would be bent around pad edge 35 to be tucked under the wound flap at its free end thereof to further assure snug engagement of the retractor with the wound flap.

As previously noted, cover 22 may be made of any suitable material such as sheet rubber or "Lyera" or other similar elastic materials. Preferably cover 22 is capable of withstanding 190° F for 3 minutes of heat sterilization. Cover 22 also has the characteristic of not carrying any electrostatic charge and should be sufficiently elastic to overcome resistance of the wound flap in its tendency to resume its normal position. Pad 20 likewise is made of a suitable material which may be easily cleaned along with cover 22 by conventional surgical cleaning operations.

Although the illustrated embodiment includes grommets at the corners of pad 20 any other suitable fastening device may be used. For example, pins may be inserted directly through the pad and cover without the necessity of pre-formed holes.

After wound flap 18 has been retracted by proper securement of retracting member 12, it is necessary in accordance with one aspect of this invention to provide some means for disposing the surgical sponges at the operative site. Such sponges are provided in tray 16 which may be of any suitable form and which includes imperforate bottom and side walls 36, 38, respectively so that water can be contained in the tray to maintain the sponges 39 (FIG. 2) such as cotton pads in a moist condition.

Since tray 16 contains water and ideally should not be overly large, it is necessary that some means be provided to maintain tray 16 in a horizontal condition whereby the water will not spill from the tray and yet the tray will still contain a sufficient amount of water and sponges.

The horizontal positioning of tray 16 is accomplished by the provision of an intermediate support member. In the preferred form of this invention support member 14 includes a completely closed fabric container 40 having a plurality of individual particles or pellets 42 therein. Such a structure could be conventionally known bean bags. Support member 14 is placed directly on top of cover 22 over pad 20. By simple adjustment the bag 40 is manipulated so that its lower surface conforms to the angulations and irregularities of retracting device 12 but the upper surface of bag 40 is made horizontal. Tray 16 is then placed directly on the horizontal upper surface of bag 40 whereby tray 16 is likewise horizontal.

Although a pellet containing bag is a preferred structure for support 14 other means such as a sponge may be used as long as it has the characteristic of having a conformable lower surface.

In accordance with this invention means are provided to assure that tray 16 will be securely mounted on support 14. Such means may take any suitable form. In the illustrated embodiment a three-sided pocket 44 is formed in the upper surface of bag 40 with pocket 44 having an open end 46. A magnet 48 is inserted into the pocket 44 through open end 46. Magnet 48 may be of conventional structure which includes an adhesive surface so that magnet 48 will be retained in place. Similarly, a corresponding magnet 50 is secured to the outer lower surface 36 of tray 16 and the magnetic force of magnets 48 and 50 cooperate to maintain tray 16 in position. Such arrangement provides for ready replacement of magnets 48, 50 in the event the magnets lose their magnetic strength or to permit the bag 40 to be sterilized. Alternatively, other suitable securing means may be provided such as formations of "Velcro" on the lower surface 36 of tray 16 and the upper surface of bag 40.

The weight of the intermediate support 14 and the tray 16 which in turn has water and sponges therein acts directly downwardly upon retracting device 12 which in turn encases the wound flap 18 with the result of the assembly also functioning hemostatically with respect to wound flap 18.

As should be apparent the inventive arrangement 10 provides an assembly which may be quickly, conveniently and securely applied in place for retracting the wound flap in a hemostatic manner and for disposing the sponges immediately at the operative site. The assembly 10 has individual elements which lend themselves to sterilization by conventional surgical techniques. Thus, the inventive arrangement effectively fulfills the previously indicated objects of the invention.

What is claimed is:

1. A surgical wound flap retractor comprising an absorbent pad member having a lower surface, a cover member partially enveloping said pad member with at least a portion of said lower surface of said pad member being exposed, said cover member including end extension sections extending beyond opposite ends of said pad member whereby said pad member may be placed directly above and in contact with an inverted wound flap with said exposed lower surface in contact therewith and said extension sections may be tucked under the wound flap to at least partially encircle the wound flap, said cover member being made of a flexible extensible non-conductive material which is capable of being heat sterilized, securing means on said pad member and cover member for maintaining said pad member in place with respect to said cover member and for permitting said device to be affixed to surgical drapery or the like, and said securing means including aligned apertures extending through said cover member and said pad member whereby fasteners may be inserted through said aligned apertures.

2. The retracting member of claim 1 including reinforcement rings in said aligned apertures, and said aligned apertures being located at the corners of said pad member.

3. The retracting member of claim 1 wherein said securing means further includes further apertures in said extension sections disposed for being aligned with said apertures when said extensions are folded under the wound flap.

4. A surgical wound flap retractor comprising an absorbent pad member having a lower surface, a cover member partially enveloping said pad member with at least a portion of said lower surface of said pad member being exposed, said cover member including end extension sections extending beyond opposite ends of said pad member whereby said pad member may be placed directly above and in contact with an inverted wound flap with said exposed lower surface in contact therewith and said extension sections may be tucked under the wound flap to at least partially encircle the wound flap, said cover member being made of a flexible extensible non-conductive material which is capable of being heat sterilized, securing means on said pad member and cover member for maintaining said pad member in place with respect to said cover member and for permitting said device to be affixed to surgical drapery or the like, a side extension section being secured to said cover member along a side of said pad member between said end extension sections, and the corresponding edges of said pad member juxtaposed to said extension sections defining hinge areas about which said extension sections may be folded.

5. A surgical wound flap retractor comprising an absorbent pad member having a lower surface, a cover member partially enveloping said pad member with at least a portion of said lower surface of said pad member being exposed, said cover member including end extension sections extending beyond opposite ends of said pad member whereby said pad member may be placed directly above and in contact with an inverted wound flap with said exposed lower surface in contact therewith and said extension sections may be tucked under the wound flap to at least partially encircle the wound flap, said cover member being made of a flexible extensible non-conductive material which is capable of being heat sterilized, securing means on said pad member and cover member for maintaining said pad member in place with respect to said cover member and for permitting said device to be affixed to surgical drapery or the like, and said securing means comprises fasteners secured to said cover member.

6. A surgical wound flap retractor comprising an absorbent pad member having a lower surface, a cover member partially enveloping said pad member with at least a portion of said lower surface of said pad member being exposed, said cover member including end extension sections extending beyond opposite ends of said pad member whereby said pad member may be placed directly above and in contact with an inverted wound flap with said exposed lower surface in contact therewith and said extension sections may be tucked under the wound flap to at least partially encircle the wound flap, said cover member being made of a flexible extensible non-conductive material which is capable of being heat sterilized, securing means on said pad member and cover member for maintaining said pad member in place with respect to said cover member and for permitting said device to be affixed to surgical drapery or the like, said cover member having an upper surface, and weighted means mounted on said upper surface of said cover member for applying pressure to the wound flap whereby said retracting device further functions hemostatically.

7. A surgical wound flap retractor comprising an absorbent pad member having a lower surface, a cover member partially enveloping said pad member with at least a portion of said lower surface of said pad member being exposed, said cover member including end extension sections extending beyond opposite ends of said pad member whereby said pad member may be placed directly above and in contact with an inverted wound flap with said exposed lower surface in contact therewith and said extension sections may be tucked under the wound flap to at least partially encircle the wound flap, said cover member being made of a flexible extensible non-conductive material which is capable of being heat sterilized, securing means on said pad member and cover member for maintaining said pad member in place with respect to said cover member and for permitting said device to be affixed to surgical drapery or the like, said cover member having an upper surface, in combination with a device for carrying sponges, said device for carrying sponges including an intermediate support member mounted on said upper surface of said cover member, said intermediate support member being made of a conformable material which is capable of having its lower surface conform to irregularities and inclinations of said upper surface of said cover member with the upper surface of said intermediate support member being substantially horizontal, and a tray mounted on said upper surface of said intermediate support whereby surgical sponges or the like may be carried in said tray.

8. The combination of claim 7 wherein said upper surface of said intermediate support member includes an open ended pocket, and said complementary attaching means comprising a first magnet in said pocket and a second magnet secured to said bottom wall of said tray.

9. The combination of claim 7 wherein said tray has a bottom wall and upstanding side walls, and said tray being imperforate and leakproof for carrying moist sponges.

10. The combination of claim 9 including complementary attaching means on said bottom wall of said tray and on said upper surface of intermediate support.

11. The combination of claim 10 wherein said intermediate support member comprises a flexible container having a plurality of pellets freely movable therein.

12. The retracting member of claim 11 wherein said complementary attaching means comprises formations of "Velcro".

13. A surgical retractor and sponge carrying assembly adapted for maintaining a wound flap retracted and for disposing sponges at the operative site comprising, in combination, a pad member for being disposed directly on the inverted wound flap for maintaining the wound flap retracted, a support member having an upper surface and a lower surface, said lower surface being pliable and conformable for fitting on said pad member and conforming to the angulations and irregularities presented by said pad member with said upper surface being substantially horizontal, and a tray mounted on said upper surface of holding surgical sponges therein.

14. The assembly of claim 13 wherein said support member is a bag containing a plurality of pellets therein.

15. The assembly of claim 13 wherein securing means are mounted to said support member and said tray for securing said tray to said support member.

16. The assembly of claim 15 wherein said securing means are removable.

* * * * *